United States Patent [19]

Piot et al.

[11] Patent Number: 5,858,339

[45] Date of Patent: *Jan. 12, 1999

[54] METHOD FOR MAKING UP THE EYES USING DEOXYRIBONUCLEIC ACID

[75] Inventors: Bertrand Piot, Colombe; Jeanne Patraud, Paris; Christian Felardos, Chevilly Larue, all of France

[73] Assignee: L'Oreal, Paris, France

[ * ] Notice: This patent issued on a continued prosecution application filed under 37 CFR 1.53(d), and is subject to the twenty year patent term provisions of 35 U.S.C. 154(a)(2).

[21] Appl. No.: 679,718

[22] Filed: Jul. 12, 1996

Related U.S. Application Data

[63] Continuation of Ser. No. 406,969, filed as PCT/FR93/00776, Mar. 29, 1995, abandoned.

[51] Int. Cl.$^6$ ............................. A61K 7/032; A61K 7/11
[52] U.S. Cl. .......................... 424/70.7; 424/63; 424/70.1
[58] Field of Search ........................... 424/70.7, 63, 401, 424/70.1

[56] References Cited

U.S. PATENT DOCUMENTS

| | | | |
|---|---|---|---|
| 4,659,562 | 4/1987 | Arraudeau et al. | 424/63 |
| 4,820,510 | 4/1989 | Arraudeau et al. | 424/63 |
| 5,116,607 | 5/1992 | Jones | 424/70 |
| 5,154,916 | 10/1992 | Arraudeau et al. | 424/63 |
| 5,283,062 | 2/1994 | Elliott | 424/401 |

FOREIGN PATENT DOCUMENTS

| | | |
|---|---|---|
| A-0106762 | 4/1984 | European Pat. Off. . |
| A-03878519 | 7/1990 | European Pat. Off. . |
| A-0416677 | 3/1991 | European Pat. Off. . |
| A-2205304 | 5/1974 | France . |
| A-2511243 | 2/1983 | France . |
| A-678489 | 9/1991 | Switzerland . |

OTHER PUBLICATIONS

Derwent Abstract of CH–A–789489, (no date).
Derwent Abstract of FR–A–2205304, (no date).
Derwent Abstract of FR–A–2511243, (no date).

*Primary Examiner*—Sally Gardner-Lane
*Attorney, Agent, or Firm*—Finnegan, Henderson, Farabow, Garrett & Dunner, L.L.P.

[57] ABSTRACT

The present invention relates to a composition which can be used in particular for eye makeup and which comprises deoxyribonucleic acid and at least one wax. The present invention also relates to a process for the preparation of the cosmetic composition and to a method of using the latter.

1 Claim, No Drawings

METHOD FOR MAKING UP THE EYES USING DEOXYRIBONUCLEIC ACID

This application is a continuation of application Ser. No. 08/406,969, filed Mar. 29, 1995, now abandoned and claims a priority of Jul. 29, 1993 under 35 USC 371 based on PCT/FR93/0076.

The present invention relates to a composition which is intended, in particular, for eye makeup and to a process for the preparation of this composition.

It is known to use waxes in eye makeup compositions. However, these compositions based essentially on wax provide a makeup of mediocre quality.

Also known is the addition of a film-forming agent of polymeric type in solution to the aqueous phase of the cosmetic composition. However, this addition is not always satisfactory in terms of the result which is obtained after application to the lashes.

It is also known to incorporate deoxyribonucleic acid into cosmetic compositions with the aim of promoting cell regeneration in the skin or for the regrowth of hair, or to stimulate antiseborrhoeic activities.

However, deoxyribonucleic acid is not known as a component in makeup compositions.

The composition according to the invention has enabled the abovementioned problems to be overcome. In particular, it has surprisingly been discovered that the addition of deoxyribonucleic acid to an eye makeup composition substantially improves the cosmetic qualities, such as the lengthening and curvature of the lashes.

The present invention relates to a composition which comprises, optionally in the presence of a cosmetically acceptable vehicle, deoxyribonucleic acid or an inorganic or organic salt thereof and at least one wax. This composition may be used advantageously for eye makeup.

The ratio by weight of the quantity of deoxyribonucleic acid to the quantity of wax may be between 0.025 and 2.5.

The molecular weight of the deoxyribonucleic acid may be between $1 \times 10^5$ and $1 \times 10^7$ daltons, preferably between $5 \times 10^5$ and $5 \times 10^6$ daltons.

The quantity of deoxyribonucleic acid may be between 0.02% and 5% by weight of dry polymer material, preferably between 0.05 and 2% by weight of dry polymer material relative to the total amount of polymers which may be present in the composition.

The waxes which are used in the makeup composition may be chosen from animal, vegetable, mineral or synthetic waxes or a mixture thereof.

The eye makeup composition may also comprise pigments chosen from inorganic and organic pigments and, optionally, nacreous pigments. These pigments are present in a proportion ranging from 3 to 25% by weight relative to the total weight of the composition, depending on the coloration and intensity of coloration which it is desired to obtain.

The composition according to the present invention may be presented in the form of emulsions such as oil-in-water or water-in-oil emulsions, in the form of a suspension in a solvent medium, in the form of microdispersions or else in solid or anhydrous paste form.

When it is used in the form of an emulsion the composition may contain surfactants which are present in a proportion of between 2 and 30% by weight relative to the total weight of the composition. These surfactants are chosen from anionic or nonionic surfactants.

The present invention also relates to a process for the preparation of the composition, which consists in mixing deoxyribonucleic acid with an oily phase containing at least one wax and, if desired, surfactants.

According to this process, the deoxyribonucleic acid may be present in an aqueous phase. A pigment may be added to the oily phase.

The components of the oily and aqueous phases may independently be dissolved or melted at a temperature of 85° C. and then mixed.

The present invention will now be described in more detail.

The deoxyribonucleic acid which is used in one of the compositions according to the invention may be either of animal or plant origin and may be in the form of one of its inorganic or organic salts. The deoxyribonucleic acid which is already used in the field of ophthalmology may be considered for the use of a composition for eye makeup, such as mascara, since this acid is very well tolerated by the eye.

The waxes chosen in the composition according to the invention generally possess a melting point of between 60 and 110° C. and have a needle penetration at 25° C. of between 3 and 40, as measured in accordance with the American standard ASTM D 5 or in accordance with the French standard NFT 004. The principle of measuring the penetration of a needle in accordance with the standards ASTM D 5 and NFT 004 consists in measuring the depth, expressed in tenths of millimeters, to which a standardized needle weighing 2.5 g penetrates when placed in a needle holder weighing 47.5 g, corresponding to a total of 50 g, the needle being placed on the wax for 5 seconds.

The waxes which may be employed in the present invention can be chosen from animal waxes, plant waxes, mineral waxes, synthetic waxes and various fractions of natural waxes, all of the waxes having the two physical characteristics mentioned above.

Among the animal waxes, mention may be made of beeswaxes, lanolin waxes and Chinese insect waxes.

Among vegetable waxes, it is possible to mention rice waxes, carnauba wax, candelilla wax and ouricury wax, cork fibre waxes, sugar cane waxes, Japan waxes, sumac wax and cotton wax.

Among inorganic waxes it is possible to mention paraffins, microcrystalline waxes, montan waxes and ozokerites.

Among synthetic waxes, it is possible to use, in particular, polyethylene waxes, waxes obtained by the Fischer and Tropsch synthesis, and waxy copolymers and their esters.

It is also possible to use hydrogenated vegetable or animal oils which in each case meet the two physical characteristics mentioned above. Among these oils, it is possible to mention hydrogenated jojoba waxes and hydrogenated oils obtained by catalytic hydrogenation of fatty substances consisting of a $C_8-C_{32}$ linear or nonlinear fatty chain, hydrogenated sunflower oil, hydrogenated castor oil, hydrogenated copra oil and hydrogenated lanolin.

The waxes which may be used according to the present invention are preferably solid and firm at temperatures below 50° C.

These waxes may be present in the form of stable dispersions of colloidal wax particles, as may be prepared by known methods such as in "Microemulsions Theory and Practice", L. M. Prince Ed., Academic Press (1977), pages 21–32.

In addition to the waxes and the deoxyribonucleic acid, the composition according to the invention may also comprise pigments chosen from inorganic pigments, organic pigments and nacreous pigments. Among inorganic pigments it is possible to use titanium dioxide (rutile or anatase) which may have been surface-treated and is codified in the Colour Index under the reference CI 77891, red, yellow and black iron oxides with the respective references CI 77499, CI 77492 and CI 77491, the manganese violet of reference CI 77742, the ultramarine blue of reference CI 77007, the chromium oxide of reference CI 77288, the chromium hydrate of reference CI 77289 and the ferric blue of reference CI 77510.

The organic pigments may be chosen from carbon black, the pigments D & C Red No. 19 of reference CI 45 170, D & C Red No. 9 of reference CI 15 585, D & C Red No. 21 of reference CI 45 380, D & C Orange No. 4 of reference CI 15 510, D & C Orange No. 5 of reference CI 45 370, D & C Red No. 28 of reference CI 45 410, D & C Red No. 13 of reference CI 15 630, D & C Red No. 57 of reference CI 15 850, D & C Yellow No. 23 of reference CI 19 140, D & C Red No. 36 of reference CI 12 085, D & C Acid Red No. 95 of reference CI 45 425, D & C Yellow No. 6 of reference CI 15 985, D & C Red No. 30 of reference CI 73 360, D & C Red No. 3 of reference CI 45 430 and the cochineal carmine-based lakes of reference CI 75 470.

The nacreous pigments may be chosen from white nacreous pigments, such as mica coated with titanium or with bismuth oxychloride, coloured nacreous pigments such as titanium-mica with iron oxides, titanium-mica with, in particular, ferric blue or chromium oxide, titanium-mica with an organic pigment of the type mentioned above, and nacreous pigments based on bismuth oxychloride.

The composition according to the invention, since it may be presented in the form of emulsions, will also comprise surfactants chosen from anionic or nonionic surfactants.

Among the anionic surfactants which may be used individually or as a mixture it is possible to mention, in particular, alkali metal salts, ammonium salts, amine salts or amino alcohol salts of the following compounds:

alkyl sulphates, alkyl ether sulphates, alkylamide sulphates and ether sulphates, alkylaryl polyether sulphates and monoglyceride sulphates, alkylsulphonates, alkylamidesulphonates, alkylarylsulphonates, olefinsulphonates and paraffinsulphonates, alkylsulphosuccinates, alkyl ether sulphosuccinates and alkylamidesulphosuccinates, alkylsulphosuccinamates,
alkylsulphoacetates and alkylpolyglycerolcarboxylates,
alkyl phosphates/alkyl ether phosphates,
alkylsarcosinates, alkylpolypeptidates, alkylamidopolypeptidates, alkylisethionates and alkyltaurates.

The alkyl radical in all of these compounds generally denotes a carbon chain comprising 12 to 18 carbon atoms.

Among the anionic surfactants it is possible to use salts of fatty acids such as oleic acid, ricinoleic acid, palmitic acid, stearic acid, the acids of copra oil or of hydrogenated copra oil, and amine salts such as amine stearates.

It is also possible to mention acyl lactates in which the acyl radical comprises 8 to 20 carbon atoms, and carboxylic acids of polyglycol ethers, corresponding to the formula:

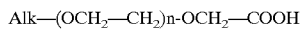

Alk—(OCH$_2$—CH$_2$)n-OCH$_2$—COOH in acid or salt form, in which the substituent Alk corresponds to a linear carbon chain having from 12 to 18 carbon atoms and in which n is an integral random value of between 5 and 15.

Among the nonionic surfactants which may be used alone or as mixtures it is possible to mention, in particular, polyethoxylated, polypropoxylated or polyglycerolated alcohols, alkylphenols and fatty acids with a fatty chain containing 8 to 18 carbon atoms.

It is also possible to mention copolymers of ethylene oxide and propylene oxide, condensation products of ethylene oxide and propylene oxide with fatty alcohols, polyethoxylated fatty amides, polyethoxylated fatty amines, ethanol amides, glycol fatty acid esters, ethoxylated or nonethoxylated sorbitan fatty acid esters, sucrose fatty acid esters, polyethylene glycol fatty acid esters, phosphoric triesters and fatty acid esters of glucose derivatives. Other compounds which may also be included in this class are the following:

the condensation products of a monoalcohol, an alpha-diol, an alkylphenol, an amide or a diglycolamide with glycidol or a glycidol precursor, such as those of the formula:

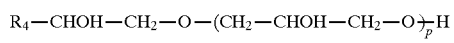

R$_4$—CHOH—CH$_2$—O—(CH$_2$—CHOH—CH$_2$—O$)_p$H in which R$_4$ denotes an aliphatic, cycloaliphatic or arylaliphatic radical preferably having between 7 and 21 carbon atoms, and mixtures thereof, it being possible for the aliphatic chains to contain ether, thioether or hydroxymethylene groups, and in which p represents an integral random value and is between 1 and 10 inclusive, as described in French Patent FR 2 091 516;

the components corresponding to the formula:

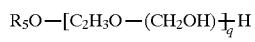

R$_5$O—[C$_2$H$_3$O—(CH$_2$OH)$]_q$H in which R$_5$ denotes an alkyl, alkenyl or alkylaryl radical and in which q is an integral random value and is between 1 and 10 inclusive, as described in the patent FR 1 477 048;

the compounds corresponding to formula:

R$_6$—CONH—CH$_2$—CH$_2$O—CH$_2$—CH$_2$—O—(CH$_2$—CHOH—CH$_2$—O$)_r$H in which R$_6$ denotes a radical or a mixture of linear or branched, saturated or unsaturated aliphatic radicals which may, if desired, contain one or more hydroxyl groups and has between 8 and 30 carbon atoms. These compounds may be of natural or synthetic origin, and r represents an integral random value of between 1 and 5 and denotes the average degree of condensation, such compounds being described in French Patent FR 2 328 763.

The composition according to the invention in the form of a nonionic emulsion consists principally of a mixture of oils and/or fatty alcohol, or else of polyethoxylated or polyglycerolated alcohols, such as polyethoxylated cetylstearyl alcohols or stearyl alcohols.

The compositions according to the invention in the form of an anionic emulsion are composed preferably on the basis of amine stearates.

The composition according to the invention may also contain ingredients which are used in cosmetics and are chosen from vitamins, trace elements, emollients, preservatives, sequestering agents, fragrances, thickeners, oils, silicones, cohesion agents, polymers and the basifying or acidifying agents which are conventionally employed in the cosmetics field, and fillers.

Among the fillers it is possible to use, in particular:

- talc, which is a hydrated magnesium silicate used in the form of particles generally smaller than 40 microns,
- micas, which are aluminosilicates of various compositions in the form of flakes having dimensions of from 2 to 200 microns, preferably from 5 to 70 microns, and a thickness of between 0.1 and 5 microns, preferably from 0.2 to 3 microns, it being possible for these micas to be of natural origin, such as muscovite, margarite, roscoelite, lipidolite and biotite, or of synthetic origin,
- starch, especially rice starch,
- kaolin, which is a hydrated aluminium silicate which is present in the form of particles of isotropic form, having dimensions which are generally less than 30 microns,
- zinc oxides and titanium oxides, which are generally used in the form of particles whose size does not exceed a few microns,
- calcium carbonate, magnesium carbonate or magnesium hydrocarbonate,
- microcrystalline cellulose, and
- powders of synthetic polymers such as polyethylene, polyesters (polyethylene isophthalate or terephthalate), polyamides such as those sold under the trade name "Nylon" or "Teflon" and silicone powders.

The thickeners included in the composition according to the invention may be chosen from natural or synthetic thickeners. Among natural thickeners it is possible to mention gums of various kinds, such as gum arabic, guar gum or carob gum.

Among synthetic thickeners it is possible to mention cellulose derivatives such as hydroxyethylcellulose, carboxymethylcellulose, starch derivatives, cellulose ether derivatives containing quaternary ammonium groups, cationic polysaccharides, salts of acrylic or methacrylic polymers, polyenes or polysiloxanes.

It is also possible to bring about thickening of the composition according to the invention by means of a mixture of polyethylene glycol and polyethylene glycol distearate and/or stearate, or by a mixture of phosphoric esters and fatty amides.

Concrete examples which illustrate, but in no way limit, the invention will now be given.

Procedure for Examples 1 And 2

The components of phase A are brought to a temperature of approximately 85° C., the components of phase B are added, and the mixture is stirred using a turbine. The water for the preparation is boiled and the preservatives are dissolved therein. At a temperature of approximately 85°, the components of phase C are added to the aqueous phase. The components of phase A, at a temperature of 80° C., are added to the aqueous phase, and are mixed in using a turbine at a temperature of approximately 30° C. in order to bring about emulsification. The components of phase D are, if appropriate, added and mixed using a blade mixer.

Procedure For Example 3

The components of phase A are melted, the pigments are added thereto and the composition is mixed. The components of phase B are mixed and are added to the components of phase A. Deoxyribonucleic acid is added to this mixture.

EXAMPLES

Example 1

Oil-In-Water Emulsion

| A | |
|---|---|
| Triethanolamine stearate | 8% |
| Glycerol stearate (sold under the name "GELEOL" by the company GATTEFOSSE) | 2% |
| Beeswax | 7% |
| Carnauba wax | 2% |
| Paraffin | 3.5% |
| B | |
| Black iron oxide | 6% |
| C | |
| Hydroxyethylcellulose (sold under the name "CELLOSIZE QP" by the company AMERCHOL) | 0.5% |
| Gum arabic | 2% |
| Hydrolysate of keratin (sold under the name "KERASOL" by the company CRODA) | 1.8% |
| Deoxyribonucleic acid (extracted from fish) (sold by the company JAVENECH) | 0.05% |
| D | |
| Panthenol | 1.0% |
| Preservative | qs |
| Water qs | 100% |

Comparative Example 1'

Oil-In-Water Emulsion

| A | |
|---|---|
| Triethanolamine stearate | 8% |
| Glycerol stearate (sold under the name "GELEOL" by the company GATTEFOSSE) | 2% |
| Beeswax | 7% |
| Carnauba wax | 2% |
| Paraffin | 3.5% |
| B | |
| Black iron oxide | 6% |
| C | |
| Hydroxyethylcellulose (sold under the name "CELLOSIZE QP" by the company AMERCHOL) | 0.5% |
| Gum arabic | 2% |
| Hydrolysate of keratin (sold under the name "KERASOL" by the company CRODA) | 1.8% |
| D | |
| Panthenol | 1.0% |
| Preservative | qs |
| Water qs | 100% |

In contrast to Example 1, this example does not contain deoxyribonucleic acid. A blind comparative test was carried out on a panel consisting of 19 women, comparing Examples 1 and 1'. The STUDENT test showed that Example 1, containing deoxyribonucleic acid, makes it possible to obtain better separation and better lengthening of the lashes after application.

Example 2

Oil-In-Water Emulsion

A

| | |
|---|---|
| Triethanolamine stearate | 10% |
| Beeswax | 8% |
| Carnauba wax | 2% |
| Paraffin | 5% |

B

| | |
|---|---|
| Black iron oxide | 5% |

C

| | |
|---|---|
| Hydroxyethylcellulose (sold under the name "CELLOSIZE QP" by the company AMERCHOL) | 1.2% |
| Deoxyribonucleic acid (extracted from wheat germ) (sold by the company INOCOSM) | 2% |
| Preservative | qs |
| Water qs | 100% |

Example 3

Dispersion

A

| | |
|---|---|
| Paraffin wax | 4% |
| Carnauba wax | 3% |
| Beeswax | 5% |
| Candelilla wax | 5% |
| Black iron oxide | 5% |

B

| | |
|---|---|
| Montmorillonite | 5% |
| Propylene carbonate | 1% |
| Isoparaffin | 55.3% |

C

| | |
|---|---|
| Deoxyribonucleic acid in water at a concentration of 3% of active substance (fish protein) (sold by the company SEDERMA) | 16.7% |

We claim:
1. A method for lengthening and curving the eyelashes which comprises applying to the eyelashes an amount of an eyelash make up composition effective to lengthen and curve the eyelashes, which composition comprises deoxyribonucleic acid or an inorganic or organic salt thereof, and at least one wax, wherein the quantity of dry deoxyribonucleic acid ranges from 0.05% to 5% by weight relative to the total weight of the composition.

* * * * *